United States Patent [19]

Anderson

[11] 4,341,120
[45] Jul. 27, 1982

[54] ULTRASONIC VOLUME MEASURING SYSTEM

[75] Inventor: Weston A. Anderson, Palo Alto, Calif.

[73] Assignee: Diasonics Cardio/Imaging, Inc., Salt Lake City, Utah

[21] Appl. No.: 92,903

[22] Filed: Nov. 9, 1979

[51] Int. Cl.³ .......................................... G01N 29/04
[52] U.S. Cl. ...................................... 73/618; 73/621; 73/633; 128/660
[58] Field of Search ................. 73/621, 620, 633, 626, 73/618; 128/660; 33/366

[56] References Cited

U.S. PATENT DOCUMENTS

| Re. 30,397 | 9/1980 | King | 128/660 |
|---|---|---|---|
| 3,727,180 | 4/1973 | Lingel et al. | 33/366 |
| 3,817,089 | 6/1974 | Eggleton et al. | 73/623 |
| 3,955,561 | 5/1976 | Eggleton | 128/660 |
| 4,094,073 | 6/1978 | Parra | 33/366 |
| 4,120,291 | 10/1978 | Paton et al. | 73/618 |

Primary Examiner—Anthony V. Ciarlante
Attorney, Agent, or Firm—Blakely, Sokoloff, Taylor & Zafman

[57] ABSTRACT

An improvement in an ultrasonic imaging system is disclosed, enabling determination of volume and/or shape of three-dimensional portions of bodily tissue or the like. The improvement is applicable to ultrasonic imaging systems of the type adapted for examining bodily tissue, especially those including sector scanning transducer means, such as electronically scanned phased arrays or mechanically scanned transducers; means for phasing the actuation of said transducers to steer the emitted sound beam in a plurality of radial directions in a fan-shaped sector; means for receiving the reflected energy from the plurality of radial directions in the sector; means for determining from the reflected energy the acoustical impedance variations within the bodily tissue examined along the radial directions and providing therefrom a reconstructed image of the fan-shaped planar cross-section of bodily tissue examined; and a transducer body for carrying said array of elements, said body having an axis aligned with the plane of said fan-shaped sector and approximately symmetrically dividing the included angle of said fan, the body being orientable with respect to the bodily tissue being examined to enable the fan-shaped sector to intersect and thereby effect imaging of a desired cross-section of said tissue. The improvement enables evaluation of the volume or shape of a three-dimensional portion of the tissue being examined, and comprises means for determining the rotational angle between a reference position and a plurality of selected examining positions of the transducer body, upon the transducer body being rotated from its reference to the selected examining positions while at least one point on the body axis remains substantially spatially fixed; and means for correlating the associated reconstructed images with the said determined angles, whereby to generate a plurality of cross-sectional images of said three-dimensional tissue portion being examined, wherein the imaged tissue cross-sections include at least one common point, thereby to enable evaluation of the volume or shape of the three-dimensional tissue portion of interest.

5 Claims, 8 Drawing Figures

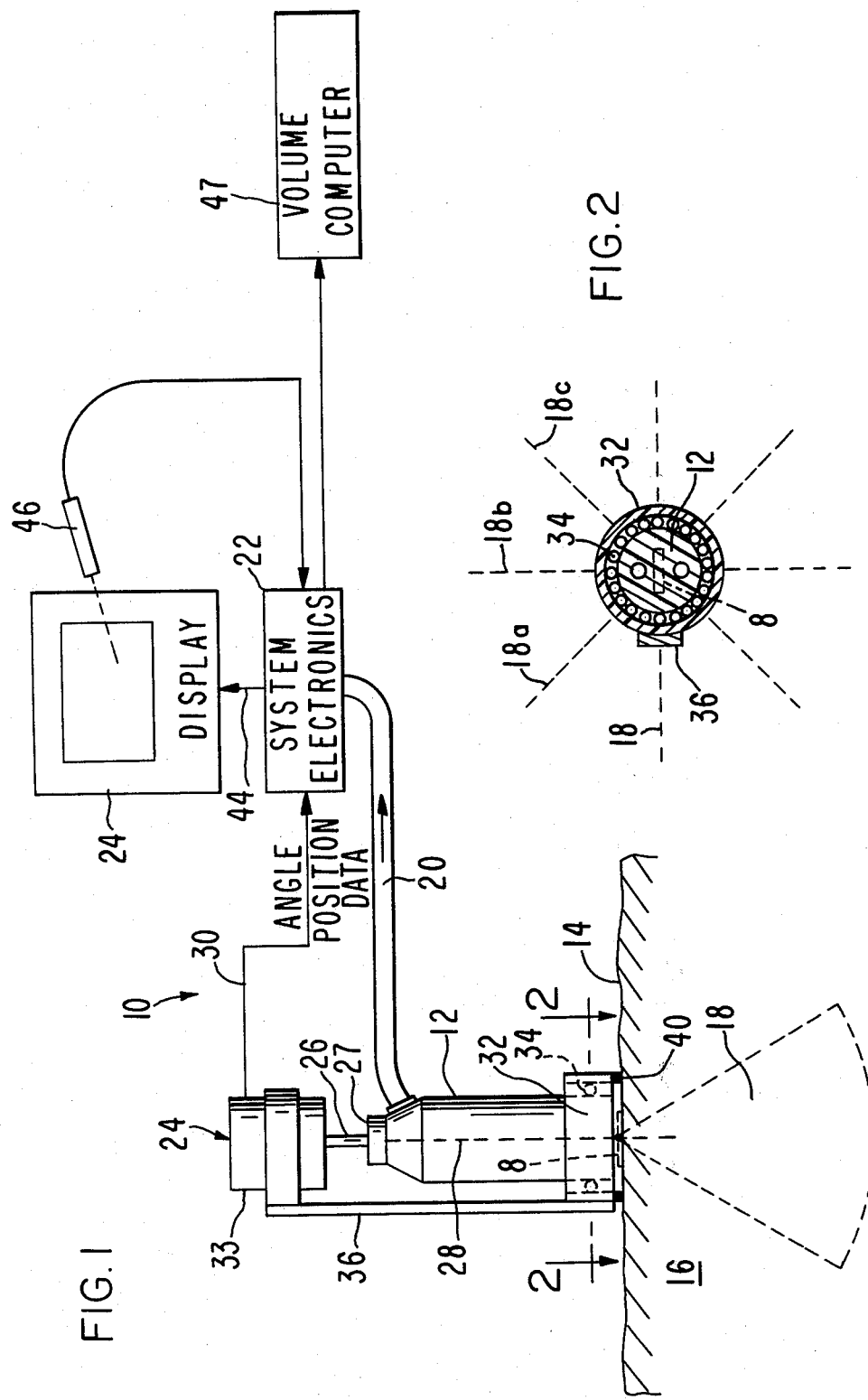

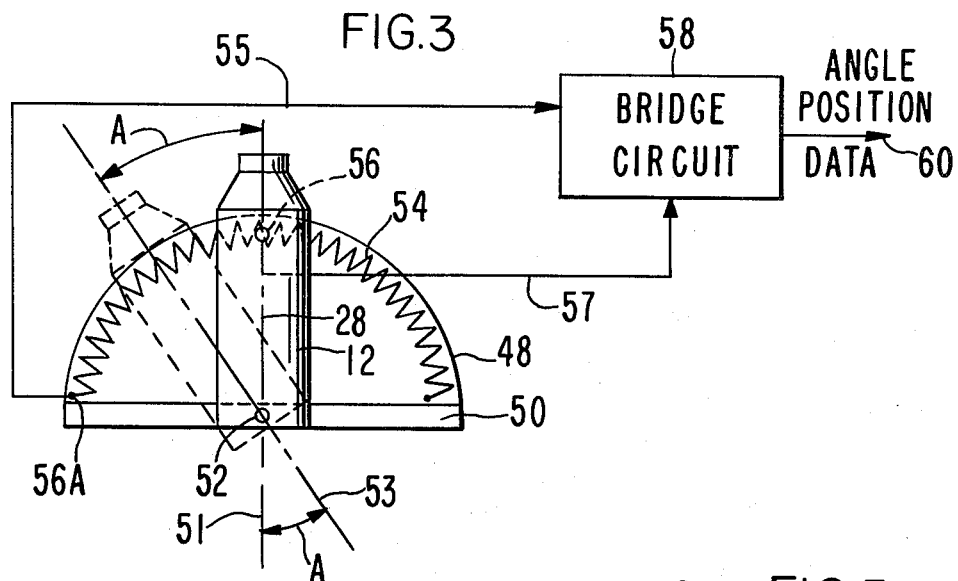
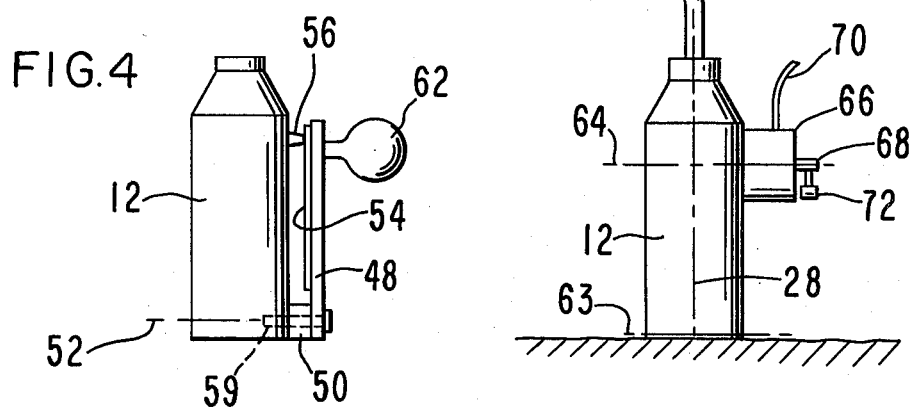
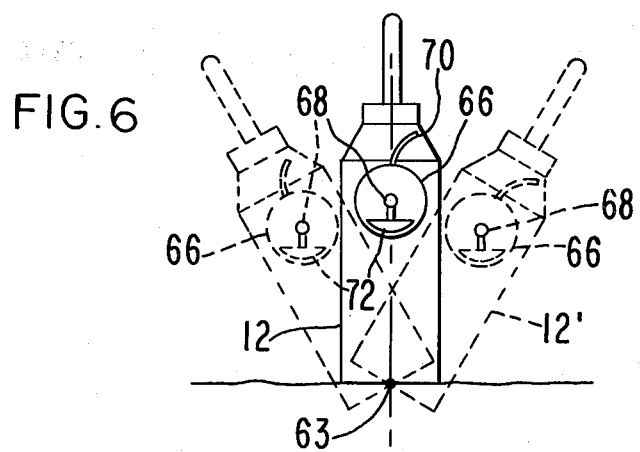

ULTRASONIC VOLUME MEASURING SYSTEM

BACKGROUND OF THE INVENTION

This invention relates generally to apparatus and methodology useful in effecting medical diagnosis, and more specifically, relates to systems and methodology utilizing ultrasonic techniques for such purposes.

Over the course of the last several decades, ultrasonic technology has played an ever-increasing role in medical diagnostics. Such techniques find application in diagnosis of various medical ailments wherein it is useful to examine internal bodily organs, with the objective of locating features or aspects of such organs which may be indicative of disease, abnormalities or so forth.

While early systems of the foregoing type included but limited capabilities and display functions, there have more recently come into use highly sophisticated devices which are capable of providing real time or recorded displays with excellent detail and good resolution of desired portions of the body being considered.

In a typical such device, and one to which the present invention is directly applicable, the transducer means and imaging system provides a cross-sectional image of an internal body portion with the transducer elements being scanned to interrogate the corresponding linear section of the body portion. Such scanning may be effected mechanically by oscillating transducer elements through said angular sector or rotating transducer elements to effect a similar result or electronically, by means of a linear array or a phased array wherein the elements, although stationary, are electronically actuated so as to produce a sound beam which scans through the interrogated cross-sectional area. In such a linear array system, a plurality of transducer elements are arranged in a side by side fashion to extend over a length of perhaps 10 to 15 centimeters. As each transducer element is activated it sends a sound beam directly into the contacting body. Any acoustical impedance variations within the body will cause some of the sound beam to be reflected back toward the transducer. The same transducer element will interrupt the returning sound energy and convert it back to electrical energy. This electrical signal is then processed and may be displayed upon a CRT screen as one line of image data. Next, the adjacent transducer element is pulsed and any reflected signals from it are displayed as an adjacent line of image data on the CRT screen. This process is repeated for each of the remaining transducer elements as a two-dimensional image is built up on the CRT screen. The final image will contain a number of parallel lines of data representing a rectangular cross-section of acoustical impedance variations within the body being examined.

In the phased array a plurality of transducer elements is arranged in compact linear fashion. Each transducer element is individually connected to a suitable transmitter and receiver, and the transmitted pulses are so phased as to steer the emitted sound beam in the desired direction. Adjustable delays provided in each receiver channel enhance the reception from the same direction as the transmitted sound beam. By suitably controlling the time of the voltages applied to the transducer elements and by controlling the adjustable delays of the separate receiver channels, the beam can be steered to any desired angle of a fan-shaped sector.

Operation of the phased array is such that a plurality of radial lines defining the fan-shaped sector are successively generated, with a relatively high number of such radial lines—typically of the order of 128 such lines—being utilized in the course of generating the entire sector. The set of such lines is generated over a short period, typically of the order of 1/30th of a second, whereby the corresponding display on the system cathode ray tube (CRT) is a high resolution, substantially real time image of the bodily portion being examined. This visualization is, in the terminology of the present art, a so-called B-mode display, i.e., one wherein variations of the acoustical impedance of the tissues are translated into brightness variations on the CRT screen.

Details regarding the prior art signal processing techniques utilized in apparatus of the foregoing type in order to generate the mentioned fan-shaped sector image are set forth in a number of points in the prior art. Reference may usefully be had, for example, to U.S. Pat. No. 4,005,382 to William Beaver, entitled "Signal Processor for Ultrasonic Imaging", which patent is assigned to the assignee of the present application.

It may further be noted that apparatus of the type to which the present invention is applicable, which apparatus is in substantial accord with the foregoing description, is available commercially from the assignee of the instant application, Varian Associates, Inc. of Palo Alto, Calif., under Model No. V-3000, which is further described as a "Phased Array Ultrasonograph".

In apparatus of the foregoing type, the linear array of transducer elements is normally carried by a transducer body, which is a hand-held or hand-manipulated probe, the longitudinal axis of which is approximately aligned with the plane of the fan-shaped ultrasonic beam, which axis therefore approximately symmetrically divides the included angle of the fan.

In a typical mode of utilization, the physician or technician performing the diagnosis places the forward sound beam-emitting end of the transducer body in contact with the body of the patient, and angulates the transducer body so as to orient its longitudinal axis at an appropriate position to obtain imaging of a desired portion of bodily tissue being examined. It will be appreciated in this connection that the fan-shaped ultrasonic beam is present in what is substantially a plane, and thus one normally examines a two-dimensional image (as for example, on the mentioned CRT screen) of the bodily tissue intersected by the said fan-shaped beam.

It will further be appreciated, that in many instances the physician or technician is not satisfied to examine cross-sections alone; his interest may reside in determining the shape or especially the volume of certain bodily organs or voids. For example, in a number of instances concerned with cardiac studies, it is highly desirable to know the volume of a heart chamber, as for example, of the left ventricle. In other types of situations, for example, in certain conditions of pregnancy, it is highly desirable to be apprised of the fetal volume.

Prior methodology using ultrasonic imaging apparatus of the foregoing type has not, however, been adequate to enable the desired volume measurements or shape determinations. Thus, it will be evident that where the transducer body is merely freely manipulated by hand, there is no known determinative relation between transducer body angularity and the resulting image; and under such circumstances the examining physician or technician can at most, effect highly qualitative evaluations, i.e, essentially such evaluator is compelled to observe the imaging screen while simultaneously changing the angle of the transducer body, without, however, having any exact information on the actual angularity.

While in some instances, apparatus of the foregoing type has been equipped with complex positioning arms for the transducer body, which enable rather precise manipulation of same, these highly bulky arrangements have different objectives than measuring volumes. In particular they are merely intended to orient the transducer body axis to enable one specific two-dimensional view. Furthermore, such arms interfere with ease of transducer manipulation by the physician or technician.

In accordance with the foregoing, it may be regarded as an object of the present invention to provide an improvement system in evaluating the volume or shape of a three-dimensional for an ultrasonic imaging system, which enables use of the said portion of the bodily tissue being examined.

SUMMARY OF THE INVENTION

Now in accordance with the present invention, the foregoing objects, and others as will become apparent in the course of the ensuing specification, are achieved in the improvement of the present invention, which is especially applicable to an ultrasonic imaging system of the type adapted for examining bodily tissue or the like, which system includes: transducer means; means for actuating said transducer means to steer the emitted sound beam to radiate a planar region within the body; means for receiving the reflected energy from the body; means for determining from the reflected energy the acoustical impedance of the bodily tissue examined along the directions of the emitted sound beams and providing from same a reconstructed image of the planar cross-section of bodily tissue examined; and a transducer body for carrying the transducer means, which body has an axis aligned with the plane of the cross-sectional region and approximately symmetrically dividing the cross-sectional region, the body further being orientable with respect to the bodily tissue being examined to enable the sound beam to intersect and thereby effect imaging of a desired cross-section of the tissue.

According to the improvement of the invention, evaluation of the volume or shape of a three-dimensional portion of the tissue being examined is possible. Such improvement comprises means for determining the rotational angles between a reference position and a plurality of selected examining positions of the transducer body, upon such body being rotated from its reference to selected positions while at least one point on the body axis remains substantially spatially fixed. Means are further provided for correlating the associated reconstructed images with the said determined angles, whereby to generate a plurality of cross-sectional images of the three-dimensional portion being examined, the said imaged cross-sections of the tissue including at least one common point, thereby to enable evaluation of the volume or shape of the three-dimensional tissue portion.

A system in accordance with the invention may include means for displaying the plurality of cross-sectional images corresponding to the determined angles and reference position, and means for evaluating at each said displayed cross-sectional image the areas of the three-dimensional portion of the image which is of interest. In addition, means are provided for computing from the areas thereby indicated for each cross-section, the approximate volume of the three-dimensional portion.

In one embodiment of the invention, the transducer body longitudinal axis is held in a fixed position, and the transducer body rotated about the said axis to successive angles at which the cross-sectional views are to be studied. A shaft encoder indicates the successive angular positions as the transducer body is rotated, with the angular position data from the encoder being provided to suitable logic. The images associated with the several angular positions are displayed and light pen or other means are used to define the outline of the portion of the image which is of interest at each of the successive cross-sections, thereby to enable area determinations. By standard computational methods, the volume of the said portion being examined may then be determined, from the areas which are indicated for each of the plural cross-sections.

In a second embodiment of the invention, the forward sound-emitting end of the transducer body is maintained in contact with the surface of the human body being examined, the transducer body being rotated about the forward point of its longitudinal axis to successive angles, to thereby produce the indicated successive planar cross-sections. An electrical contact point at the upper portion of the transducer body, may in this instance be maintained in contact with a resistive path forming part of a bridge circuit, to thereby provide a measure of the transducer angle.

A further embodiment of the invention is the same as the second embodiment but in this instance, a shaft encoder is utilized to indicate angularity, with the shaft projection of such encoder having a weighted element secured thereto to hold the encoder shaft projection at a reference position corresponding to a vertical orientation of the said weight means. Differing degrees of angularity are thus measured by rotational displacement of the transducer body from the vertical.

BRIEF DESCRIPTION OF THE DRAWINGS

The invention is diagrammatically illustrated, by way of example, in the drawings appended hereto, in which:

FIG. 1 is a schematic diagram of a first embodiment of a system in accordance with the present invention, wherein the transducer body and immediately contiguous elements are shown in elevation;

FIG. 2 is a transverse cross-sectional view of the transducer body of FIG. 1, taken along the line 2—2 of FIG. 1;

FIG. 3 is a diagrammatic and schematic view similar to FIG. 1, but depicting a second embodiment of the invention;

FIG. 4 is a side elevational view of a transducer body and associated elements of FIG. 3;

FIG. 5 is a side elevational view of a transducer and associated elements, forming part of a third embodiment of the invention;

FIG. 6 is a side elevational view of the apparatus portions depicted in FIG. 5, and illustrating functioning of same as the transducer body is angulated;

DESCRIPTION OF PREFERRED EMBODIMENT

Figure 7:
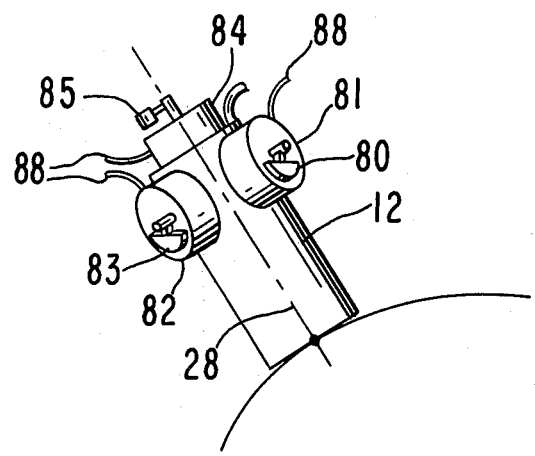
FIG. 7 is a side elevational view similar to FIG. 6, but depicting another embodiment of the invention, in which further modes of angulation of the transducer are considered.

In FIGS. 1 and 2 herein, a system 10 in accordance with the present invention is set forth. The imaging system 10, with the exception of the specific elements shown in the Figure and now to be discussed, generally conforms to the ultrasonic imaging systems of the prior art which have been discussed in the "Background" portion of this specification, and which are exemplified in one commercial embodiment by the aforementioned Varian Associates Model V-3000 "Phased Array Ultrasonograph". Such system thus includes a linearly arranged array of side-by-side transducers, which array is mounted in known manner toward the lower end 8 of a transducer-carrying body 12, which in many systems of the prior art is manually manipulated and typically held in good acoustic contact with the skin 14 of a human subject whose underlying tissues 16 are sought to be examined. In practice, a coupling gel is commonly used to form a good acoustical coupling between the transducer surface and the skin of the subject.

These tissues 16 can, of course, include various internal organs and the like. For example, in a typical case the skin 14 may overlie the chest or abdominal cavity, and it is the heart or other internal organs which are desired to be examined—by manipulation of the transducer body 12, which enables the generally fan-shaped ultrasonic beam 18 to be projected into the cavity or other tissue portions where an examination is desired. Again, as previously discussed, the linear array of transducers is phased in operation to cause the emitted sound pulses to be directed along line or radial elements in the fan beam 18, with the reception from the transducer elements being appropriately actuated as to enchance reception from the desired directions, so that the fan beam is effectively composed of a series of radial lines along which information is obtained. Additional discussion of this type of apparatus, and additional illustration of same, may be found in such articles as "Cardio-Vascular Diagnosis with Real Time Ultrasound Imaging", by O. T. Vonn Ramm, et al., which article appears in Volume 6 of *Acoustical Holography*, Edited by Newell Booth, Plenum Press, New York, 1975.

Although the present FIG. 1 embodiment makes use of a phased aray transducer means, it will be appreciated that the fan-shaped sector scan could also be created by a mechanically scanned transducer, as mentioned above in the Background of the Invention. An alternative embodiment in which such a mechanically scanned fan-shaped sector soundbeam format is developed by means of rotating transducer elements will be described below in connection with FIG. 8. Indeed, the benefits of the invention are also applicable to the simplest static imaging system in which no fan-shaped sector format is developed and to other cross-sectional imaging systems such as the linear array system which forms a rectangular-shaped soundbeam format.

Pursuant to the usual operation of systems of the FIG. 1 type, the acoustical signal data proceeds via a connecting cable 20 to system electronics 22, which generates the appropriate signals for the transducer and appropriately processes the return signals from the transducers, as known in the art, and may provide data to a display means 24. The latter typically comprises a CRT where visual display is desired, although other possibilities are known where permanent records or the like are required. Again it is emphasized that as thus far discussed, all such elements are well-known in the prior art.

In accordance with the present invention, a shaft encoder 24 is secured at the rearward end 27 of transducer body 12, with its projecting and rotatable shaft 26 being aligned with the longitudinal axis 28 of body 12. The shaft axis 26 is rigidly secured to the rearward end 27 of body 12, in consequence of which, upon rotation of body 12 about axis 28, the shaft 26 is made to rotate with same.

Shaft encoder 24 may be a standard "off-the-shelf" type of device, numerous types of which are available and well known in the electronics and related art. Suitable devices of this type are, for example, available under the trademark "Rotaswitch", from Disc Instruments, Inc. of Costa Mesa, Calif. As is known in the pertinent art, encoder devices of this type can permit a determination of the precise direction and degree of rotation of the associated shaft, and thus provide an output signal, in the present instance via a line 30, which is specifically indicative of the angular position of the rotated shaft with respect to a reference position.

In the present system 10 it is seen that the lower or forward end 8 of transducer body 12, is surrounded by an annular collar 32, with an intervening bearing 34. Collar 32, in turn, is rigidly connected via a member 36 to the body 33 of encoder 24. Preferably, the lower or forward end of the collar 32 is provided with a ring 40 having high friction characteristics, such as rubber or the like.

In consequence of the foregoing arrangement, it will be clear that when transducer body 12 is placed with its forward sound projecting end 8 in good acoustic contact with the skin 14, the collar 32 including the friction ring 40, will similarly bear against the skin surface. In consequence, the operator may now proceed to effect rotation of body 12 about its longitudinal axis 28. The outer cage-like portion defined by coller 32, member 36, and the rigidly-connected encoder body 33 remain, however, stationary as rotation of body 12 is effected, with consequent turning of shaft 26.

By virtue of this arrangement, it will be clear that the projected fan beam 18, which initially may be oriented as shown in FIG. 1 and at FIG. 2, may be rotated through successive angular positions—as suggested at 18A, 18B, and 18C in the transverse cross-sectional orientation, perpendicular to axis 28, of FIG. 2. As this operation is effected, however, the angular position data is provided via line 30 to system electronics 22. Simultaneously, the display at 24, which receives its input through line 44 from system electronics 22, changes with the specific rotational angle of body 12. Such angle may further, if desired, be provided directly to the display means whereby the operator may be apprised of the exact rotational angle at which the view is seen.

With the aid of the foregoing, it may be directly appreciated how a volume of tissue imaged at display 24 may be examined and evaluated. In particular, the operator rotates transducer body 12 while simultaneously observing display 24 which may indicate the angle associated with the display on view. For example, such displays may be effected at each successive 1° position.

While this arrangement enables the operator to make direct visual estimates of the shape or volume of the tissue portion being examined, a more precise scheme is enabled. In particular, a light pen means 46 or other device may be provided, which means is utilized to determine areas at each successive angular position selected in accordance with a pre-set program, as for example, each 10°. The operator thus stops the rotation of body 12, e.g., 10°, 20°, 30°, etc., and using the light pen means 46 may delineate the perimeter of the tissue portion deemed of interest. Thus, for example, if the left ventricle of the heart is being examined and its volume being ascertained, the operator at each 10° or other pre-set position, may use the light pen to delineate the outline of the said ventricle for that particular cross-section. The image may be maintained at a selected point in the cardiac cycle by suitable triggering from the R-wave of the electrocardiagram as is well-known in the art. By use of suitable screen coordinates the outline of the area of interest may be expressed as a series of digitized coordinates. The signal from the light pen means 46 is thus provided to system electronics 22, and thence to a volume computer 47, whereby by application of standard numerical techniques, the volume of the entire void or tissue portion may be ascertained by numerical processing of the successive areas calculated for a full 180° sweep of successive sections through the void or tissue being evaluated.

In FIGS. 3 and 4 herein, a second embodiment of the present invention is set forth. In this instance, the basic operation of the transducer and imaging system is similar to that which has been described in connection with FIG. 1. with the transducer body 12 being as previously described. In the present instance, however, the said transducer body is not rotated about its longitudinal axis 28 but rather about a line 52 which is transverse to the longitudinal axis 28, and residing (during use) approximately adjacent to the surface of the skin. In this instance, it is thus contemplated that the transducer body 12 will be rotated through angles A of varying and successive values, in order to again produce successive cross-sections through the underlying tissue as previously discussed. The plane of the fan beam is perpendicular to the plane of the drawing, and is indicated by line 51 when the transducer body 12 is perpendicular to the skin surface, and by line 53 when transducer body 12 has been rotated about line 52 by angle A.

In the present instance, instead of utilizing a shaft encoder as heretofore discussed, a semi-circular resistive track 54 is provided, with an electrical contact slider point 56 (see FIG. 4) at one side of transducer body 12 being maintained in contact with the resistive track 54. Resistive track is mounted upon an upstanding support 48 with platform 50 attached to the base of support 48. Platform 50 is held flat against the surface of the skin by handle means 62. Transducer body 12 is mounted for rotation about line 52 via axle support 59. One end 56A of resistive track 54 is connected via line 55 to one leg of a bridge circuit 58, with the sliding contact point 56 proceeding via line 57 to the other end of the same leg of the bridge circuit. By application of standard bridge circuitry techniques, the degree of angularity A of transducer body 12 may be directly ascertained, as body 12 is rotated about line 52 via axle support 59. Thus once again an angle position data signal is provided from bridge circuit 58 at output 60 which can be provided to system electronics 22 and processed as aforementioned. During rotation of the body 12 to its successive angular positions, the apparatus can be conveniently positioned and maintained by handle means 62.

In FIGS. 5 and 6, a yet further embodiment of the invention is set forth. In this instance the body 12 is again rotated about a line 63 along and in contact with the skin surface. This line again intersects the longitudinal axis 28 of body 12. Thus, in the present instance, the transducer body 12 can be rotated to successive angular positions about an axis of rotation coinciding with line 63.

In order to determine the degree of angularity in the embodiment of FIGS. 5 and 6, a further shaft encoder 66 is utilized, which can be of the same general type discussed in connection with FIG. 1. In the present instance, the shaft encoder 66 is secured to one side of transducer body 12. The axis 64 of the shaft 68 of the encoder is parallel to line 63. The shaft 68 of the encoder has secured thereto a weight 72, which weight will tend to be oriented at its lowermost point, i.e., as the body 12 is angulated, as for example to the position 12' shown in FIG. 6, the weight will tend to remain in its lowermost position, causing the shaft 68 to rotate slightly to maintain such attitude. Thus, it will be evident that again the rotation of the shaft 68 of encoder 66 will provide a direct indication of the angular position of body 12, which provides angle position data via a line 70, proceeding again to system electronics 22, where it may be processed as aforementioned to ultimately provide volume computation or the like.

In a further embodiment of the invention, the transducer body is angulated back and forth to cause the cross-sectional area being observed to be rotated about line 63 in contact with the skin surface. The line 63 is parallel with encoder shaft 68.

FIG. 7 illustrates a transducer which incorporates three encoders similar to those illustrated in FIGS. 5 and 6. Encoders 81 and 82 are mounted at right angles to the transducer axis 28 and at right angles to each other thereby providing information with respect to the vertical of the fan plane and also indicate any angular motion take place within the image plane itself. In addition, angle encoder 84 can be used in cases where the transducer axis 28 is not aligned along the vertical direction to indicate any rotation about axis 28. The angular positions of these three encoders are provided via data lines 88 to system electronics 22 where it may be processed as aforementioned to provide volume computation or the like.

Figure 8:
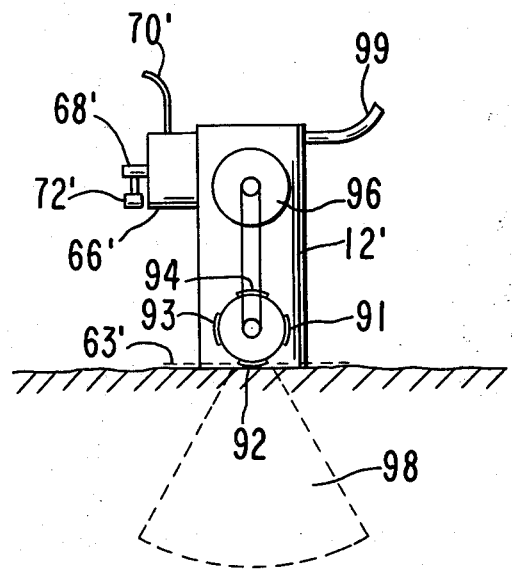
FIG. 8 is a side elevational view of a transducer body and its sector scan pattern in which said sector format is developed by the mechanical scanning of transducer elements.

FIG. 8 is illustrative of systems that employ mechanical scanning to develop a sector format in contrast to the above described systems which used an electronic steered array. In this system four transducer elements 91, 92, 93 and 94 are mounted on the periphery of a wheel which is driven by motor 96. As each transducer element is rotated through the desired sector region 98, the transducer is activated by a series of pulses to send out acoustical beams into the tissue within region 98 and echoes therefrom are received by the same transducer and coupled via line 99 to the systems electronics 22. As in the case illustrated in FIG. 5, encoder 66' with shaft 68' and weight 72' will provide a direct indication of the angular position of transducer body 12' with respect to the vertical. Thus the angular orientation of the scan plane 98 can be determined with respect to the vertical so that as the transducer body 12' is rotated about axis 63' which is parallel to shaft axis 68', the relative orientation of these various scan planes is determined. This information is coupled to the system electronics via line 70'.

While the present invention has been particularly set forth in terms of specific embodiments thereof, it will be understood in view of the instant disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

I claim:

1. In an ultrasonic imaging system of the type adapted for examining bodily tissue or the like; said system including a transducer means interrogating said bodily tissue to be examined with an ultrasonic beam which is swept over an internal fan shaped sector of said tissue to be examined; means for determining from the reflected ultrasonic energy resulting from said beam the variations in acoustical impedance of said bodily tissue over the area of said sector and providing therefrom a reconstructed image of a cross-section of bodily tissue corresponding to said sector; said transducer means including a housing body, said body including a longitudinal axis approximately aligned with the plane of said fan-shaped sector and approximately symmetrically dividing the included angle of said fan, and said body being orientable with respect to the bodily tissue being examined to enable said fanshaped sector to intersect and thereby effect imaging of a desired cross-section of said tissue; the improvement enabling evaluation of the volume or shape of a three-dimensional portion of the tissue being examined, comprising:

means for determining the rotational angle between a reference position and a plurality of selected examining positions of said transducer body, upon said transducer body being rotated from said reference to said selected positions while at least one point of said longitudinal axis remains substantially spatially fixed, said means for determining comprising a shaft encoder means mounted to said body for providing a signal indicative of said rotational angle; means for correlating the associated reconstructed images with the said determined angles, whereby to generate a plurality of cross-sectional images of said three-dimensional tissue portion being examined, wherein the imaged tissue cross-sections include at least one common point, thereby to enable evaluation of the volume or shape of the said three dimensional tissue portion; and means for supporting said transducer body for rotation about said longitudinal axis.

2. A system in accordance with claim 1, including means for displaying the plurality of cross-sectional images corresponding to said determined angles and said reference position; and means for computing from the areas thereby indicated for each said cross-section, the approximate volume of the said three-dimensional portion of interest.

3. A system in accordance with claim 1, in which said transducer means includes at least one transducer element which is mechanically scanned over an arc, whereby said beam is swept over an internal cross-sectional area which is a fan-shaped sector of said tissue being examined.

4. A system in accordance with claim 1, in which said transducer means is a phased array of transducer elements which emits said ultrasound beam and which scans said beam over said internal cross-sectional area in a fan-shaped sector.

5. A system in accordance with claim 1 in which said transducer means is a linear array of transducer elements emitting said ultrasound beam and scanning said beam over a rectangular internal cross-sectional area.

* * * * *